United States Patent
Abels

(10) Patent No.: US 6,220,857 B1
(45) Date of Patent: Apr. 24, 2001

(54) ORTHODONTIC FASTENING ELEMENT

(76) Inventor: Norbert Abels, Alleestr. 30 A, 66424 Homburg (DE)

( * ) Notice: Subject to any disclaimer, the term of this patent is extended or adjusted under 35 U.S.C. 154(b) by 0 days.

(21) Appl. No.: 09/424,102

(22) PCT Filed: Mar. 18, 1999

(86) PCT No.: PCT/EP99/01814

§ 371 Date: Dec. 21, 1999

§ 102(e) Date: Dec. 21, 1999

(87) PCT Pub. No.: WO99/47064

PCT Pub. Date: Sep. 23, 1999

(30) Foreign Application Priority Data

Mar. 19, 1998 (DE) .............................................. 198 12 184

(51) Int. Cl.[7] .................................................. A61C 7/12
(52) U.S. Cl. ................................................ 433/8; 433/10
(58) Field of Search ................................ 433/2, 8, 9, 10, 433/11, 13, 22

(56) References Cited

U.S. PATENT DOCUMENTS

| | | | |
|---|---|---|---|
| 3,128,552 | * 4/1964 | Broussard . | |
| 4,279,593 | * 7/1981 | Röhlcke | 433/8 |
| 4,527,975 | * 7/1985 | Ghafart et al. | 433/8 |
| 4,559,013 | * 12/1985 | Amstutz et al. | 433/22 |
| 4,597,739 | * 7/1986 | Rosenberg | 433/16 |
| 4,687,441 | * 8/1987 | Klepacki | 433/9 |
| 4,712,999 | 12/1987 | Rosenberg | 433/8 |
| 4,913,654 | * 4/1990 | Morgan et al. | 433/8 |
| 5,037,296 | * 8/1991 | Karwoski | 433/8 |
| 5,078,596 | 1/1992 | Carberry et al. | 433/8 |
| 5,125,832 | * 6/1992 | Kesling | 433/8 |
| 5,160,260 | * 11/1992 | Chang | 433/8 |
| 5,224,858 | 7/1993 | Hanson | 433/10 |
| 5,556,276 | * 9/1996 | Roman et al. | 433/8 |

FOREIGN PATENT DOCUMENTS

| | | |
|---|---|---|
| 23 57 573 C2 | 7/1982 | (DE) . |
| 91 12 872 U | 2/1992 | (DE) . |
| 296 08 349 U1 | 11/1996 | (DE) . |
| 714639 | 5/1996 | (EP) . |
| WO 94 00072 | 1/1994 | (WO) . |

* cited by examiner

Primary Examiner—Ralph A. Lewis
(74) Attorney, Agent, or Firm—Gifford, Krass, Groh, Sprinkle, Anderson & Citkowski, P.C.

(57) ABSTRACT

An orthodontic securing element has a base and at least one holder which is arranged on the base. A cover which covers over the base and the holder is secured to the base.

10 Claims, 3 Drawing Sheets

ORTHODONTIC FASTENING ELEMENT

BACKGROUND OF THE INVENTION

1. Field of the Invention

The present invention relates to an orthodontic securing element for orthodontic therapy, which is also called a bracket.

2. Reference to Related Art

A large number of juvenile and adult patients are treated orthodontically for correcting existing dysgnathias. In order to achieve the goal of the treatment as rapidly as possible and to the full extent planned, and also in order to be less dependent on the cooperation of the patient and to realize somatic tooth movements, firmly seated orthodontic apparatuses are in use.

The disadvantages of firmly seated apparatuses of this kind, such as brackets and bands, are a substantially more difficult oral hygiene (removal of calcium in the region of the brackets) and also a significantly reduced wearing comfort which is caused by the brackets which have been used up to now. Food residues remain around the brackets with bacterial settlement (plaque lawn and subsequent formation of caries) as a result, with the acids thereby arising causing decalcinations of the hard tooth substances, which leads as a result to destruction of the hard tooth substance. In addition mouth odors, the presence of which is very disagreeable for the patients wearing the apparatus, arise through the bacterial settlement and through the decomposing food residues. In addition conventional brackets have proved disadvantageous in so far as they offer an insufficient wearing comfort, can cause injuries to the lips, tongue and cheeks and negatively influence the lingual technique.

The problem (object) on which the invention is based is to create an orthodontic securing element (bracket) which has a greater wearing comfort.

SUMMARY OF THE INVENTION

This object is satisfied through an orthodontic securing element having a base and at least one holder which is arranged on the base, with a cover which covers over the base and the holder being secured to the base.

In accordance with the invention a preferably hood-like cover is placed onto the entire bracket so that the previously used parts of the holder, which have edges, are covered. Through this the required parts of the holder, for example slots, bracket wings, hooks and the like are hidden beneath the cover so that lips, cheeks or the tongue are not injured or irritated by these elements. Through a smooth and arched execution of the cover the self cleaning mechanism of the teeth is in addition substantially less impaired.

A further advantage of the complete cover of the securing element in accordance with the invention lies in the lower susceptibility to bacterial contamination. Through the cover in accordance with the invention all angles, edges and niches of the securing element or of its holder respectively are covered over with respect to the oral cavity so that no food residues can become fixed there and a bacterial attack is significantly reduced.

Advantageous further developments of the invention are described in the description, in the drawings and in the subordinate claims.

In accordance with a first advantageous embodiment the contour of the edge of the cover corresponds to the outer contour of the base of the securing element. Thus in this embodiment the entire bracket is substantially completely covered over by the cover so that the wearing comfort is optimized.

The cover is preferably executed to be hood-like and has no disturbing corners or edges. In this a convex curvature with radii of curvature which are as large as possible is preferred, since a shape of this kind is felt to be the least disturbing. Through a continuously arched surface both the bacterial attack and the irritation of the oral cavity are minimized.

The cover is preferably closed with the exception of two openings for passing a bow through, with the openings preferably being matched to the cross-section of the bow. Thus in this embodiment as well it is ensured that no food residues can penetrate under the cover in the region of the openings through which the bow is passed.

In order to enable a simple placing on of the cover onto the bracket with a bow secured thereto, the cover can in an advantageous manner be formed to be slit in the region of the openings. Through this the cover, which is preferably manufactured of an elastic material, can be briefly opened in the region of the slits so that the cover can be placed onto the base, with it being possible for the bow after being placed on to emerge through the openings which are provided. After the placing on the cover closes as a result of its elastic properties so that the bracket is completely protected in the direction of the oral cavity.

In accordance with a further advantageous embodiment of the invention the base has at its outer periphery a circumferential ledge, onto which the cover can be placed on. In this way the transition between the outer surface of the cover and the tooth surface can be formed without edges, with a good sealing between the base and the cover being ensured at the same time.

The base preferably has rounded off corners or is executed substantially ovally or elliptically respectively. Through a shaping of this kind disturbing corners or edges are also avoided in the region of the base, which further increases the wearing comfort.

The cover can be hingably secured to the base or be placeable onto the base, for example through a clamping seating. It is also possible to secure the cover through adhesive bonding.

In order to facilitate a measurement of the bracket position with a camera and a computer system, one or more registering aid devices can furthermore be arranged within the cover, for example at the holder, which are used as reference points.

In accordance with a further advantageous embodiment of the invention one or more hooks are arranged at the securing element which are likewise protected by the cover. In order for example to move teeth in a specific direction, these hooks can be folded out in accordance with the invention so that they project beyond the outer contour of the base and are easy to reach there. The hooks likewise have a rounded off and thus non disturbing outer contour. After the desired moving of the teeth the hooks can be moved back again so that the cover can be placed on onto the base.

In certain uses it can be advantageous to provide an additional opening for the passage through of the hook. This opening can for example be formed by a punched part which is broken out only when required. A renewed closing, for example through pivotal connection with the help of a film hinge or the like is also possible. In this case the hook can be used without it being necessary for the cover to be taken off.

In order to enable a rigid connection between palate bows and for example two premolars each as anchoring teeth, a connection mechanism between the palate bow and the bracket is provided in accordance with a further embodiment. Furthermore, a slit, which is also called a slot, and which serves for receiving the bow, is provided within the bracket. This slot has a reversible, individually insertable holding mechanism for the bow, so that the most diverse of orthodontic anchoring tasks can be solved.

In accordance with a further aspect of the present invention at least the outer surface of the cover has self cleaning properties, which has not previously been used in dental medicine for brackets. Self cleaning materials are known in principle and have a self cleaning effect which exploits the so-called "lotus effect" and which is achieved through a surface with a predetermined roughness. Through this preset roughness, polar and nonpolar liquids can run off the surface in droplets, without residues, with contamination particles being taken along in the process (cf. C. Neinhuis and W. Barthlott, 1997: Characterisation and distribution of water-repellent, self cleaning plant surfaces. Annals of Botany 79).

The self cleaning properties can preferably be achieved through an anti adhesion coating, for example of a sol-gel material. Sol-gel materials of this kind can be manufactured by a wet chemical method in which, starting from a liquid colloid-disperse system a reaction is initiated which leads to the build-up of a three dimensional network. For example silicic acid esters or metal alkoxides, which react through hydrolysis and condensation to form an inorganic network, can be used as starting compounds. Through this, repellent surfaces can be produced which have the desired self cleaning properties.

Preferably, not only the outer surface of the cover, but also the entire securing element is provided with an anti adhesive coating, with it not being necessary to equip the lower side of the base, which is secured at a tooth, with a coating of this kind.

In accordance with a further aspect of the present invention, storage locations for bacteriostatic and/or bactericidal substances are provided at the securing element and inside the cover. Gels or pastes with bacteriostatic or bactericidal action can be introduced into these storage locations, for example cavities. Silver-fluorine compounds, phenol compounds and the like come under consideration as bactericidal substances.

The present invention relates not only to an orthodontic securing element, but also to the described cover, with which conventional brackets can be subsequently equipped.

BRIEF DESCRIPTION OF THE DRAWINGS

In the following the present invention will be explained in a purely exemplary manner with reference to the accompanying drawings and with reference to an advantageous embodiment. Shown are:

FIG. 2 the securing element of FIG. 1 with the cover placed on; and

Figure 1:
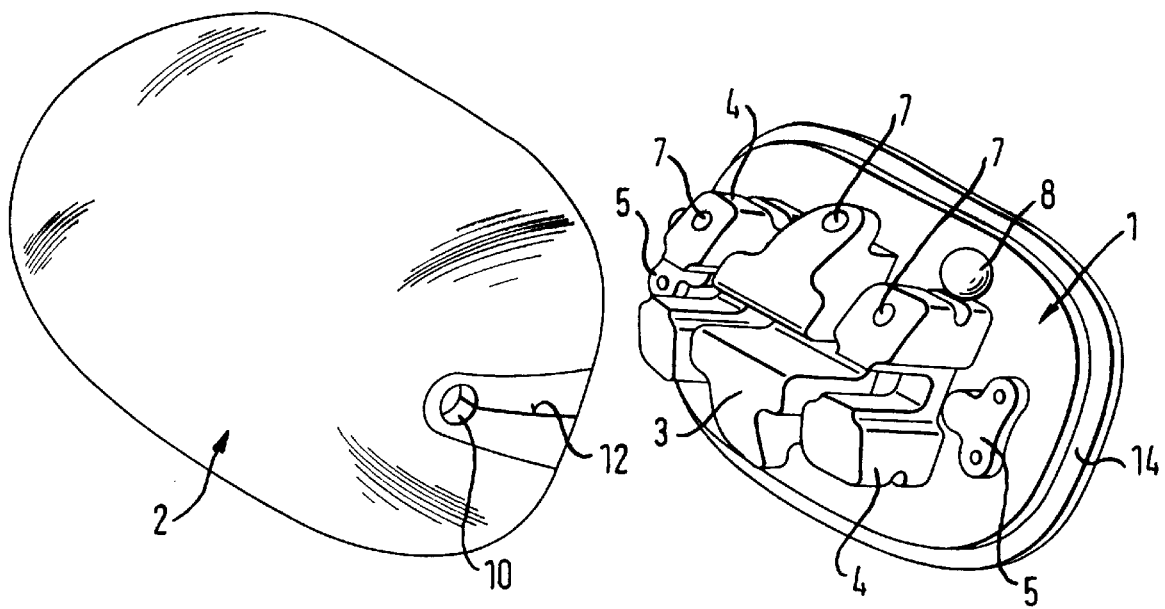
FIG. 1 a perspective illustration of a securing element with the associated cover.

The orthodontic securing element illustrated in the figures, also called a bracket, has a base 1 on which a holder for a bow is arranged. The holder has an insertable, reversible bow holder mechanism 3, 4 so that the most diverse of orthodontic anchoring tasks can be solved.

The base 1 is executed substantially rectangularly, but has strongly rounded off corners. At the two narrow sides of the base, an inner rotation wing 5 for the derotation of teeth is in each case secured on the former. Furthermore, a registering aid device 7 is arranged on each of the individual elements 3, 4 of the bow holder mechanism and enables a measurement using a camera and a computer system. Furthermore, at the element 4 of the bow holder mechanism at the right in FIG. 1 a hook 8 is provided which can be folded out in order to move teeth in a specific direction.

Figure 3:
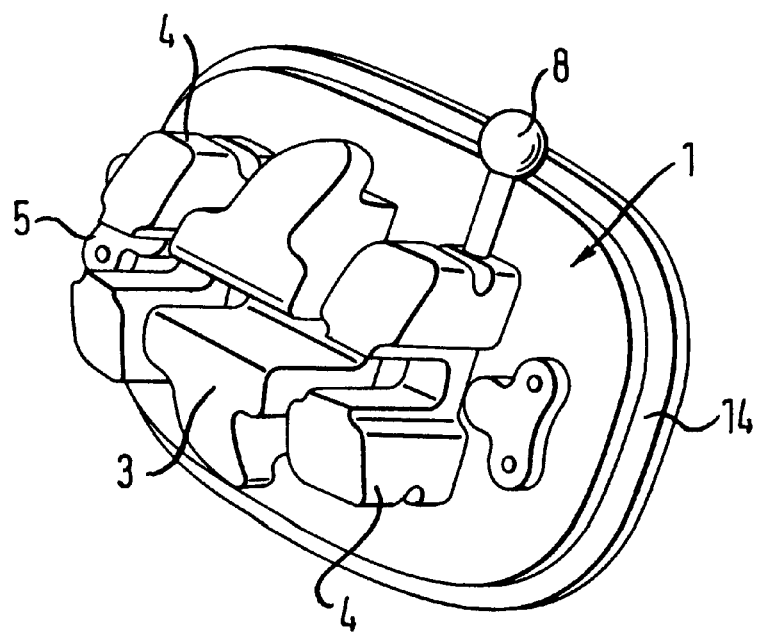
FIG. 3 the securing element of FIG. 1 without the cover and with drawn out hook.

FIG. 3 shows this hook 8 in the folded out state. In this position an intervention can be carried out at the hook in order to achieve a desired displacement of the teeth. As FIG. 3 further shows, the hook 8 projects with its sphere-like end beyond the outer contour of the base 1. In the folded in or pushed in state respectively the end of the hook 8 is located inside the outer contour of the base 1 (cf. FIG. 1).

As FIGS. 1 and 3 further show, a slit is formed through the bow holder mechanism 3, 4 which serves for the accommodation of the bow (not illustrated). In this the bow is inserted into the slit and arrested there.

FIG. 1 furthermore shows the cover 2 which is provided in accordance with the invention and which can be secured to the base 1. This cover 2 is manufactured of plastic and executed in the manner of a hood without disturbing corners or edges. The outer surface of the cover 2 always extends so as to be convexly arched, with the contour of the edge of the cover 2 corresponding to the outer contour of the base 1.

Figure 2:
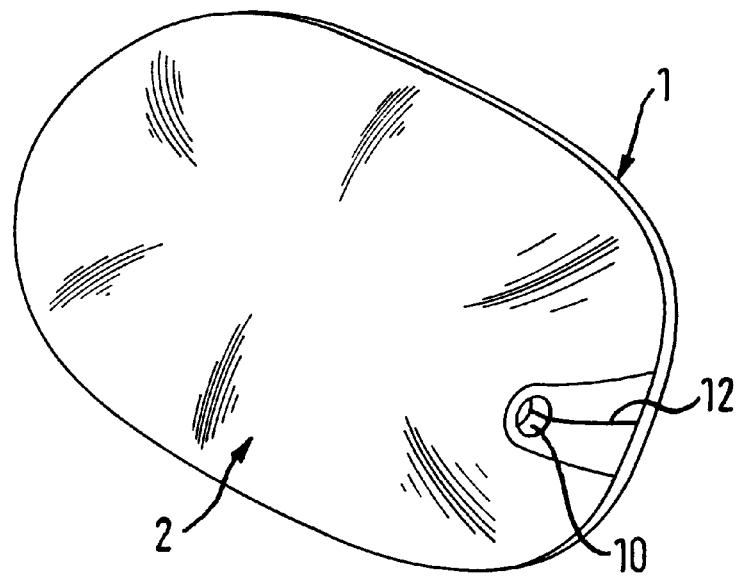

As FIG. 2 shows, the cover 2 is placed onto the base 1 and in this state completely covers over the base 1 and the holder 3, 4 which is mounted thereon as well as the rotation wings 5 and the hook 8 which can be folded in. In this state the space which is enclosed between the base 1 and the cover 2 is closed with the exception of two openings 10 (in FIGS. 1 and 2 only one opening can be recognized), which serve for passing the bow through. The two mutually oppositely lying openings 10 are arranged approximately centrally at the two narrow sides of the cover 2, with the cross-section of the openings 10 being matched to the cross-section of the bow. In order to enable a placing on of the cover 2 onto the base 1 when the bow is inserted into the securing element, the cover 2 is formed to be slit in the region of the openings 10. For this a slit 12 extends in each case rectilinearly from the opening 10 at right angles up to the outer edge of the cover 2. As a result of the elastic execution of the plastic cover 2 the slit 12 is normally closed. The latter can however be opened through a gentle pushing apart of the longitudinal sides of the cover when placing on the cover 2 so that the bow can be passed through the slit 12 into the opening 10. Then the slit 12 closes up again, through which at the same time the cover 2 is held on the base 1 by the bow.

As FIGS. 1 to 3 further show, the base 1 has at its outer periphery a circumferential ledge 14, onto which the outer edge of the cover 2 is placed. In the placed on state the transition between the outer surface of the cover 2 and the tooth surface is free from edges, which means that the outer surface of the cover 2 merges continuously and smoothly into the outer end side of the ledge 14.

All elements of the securing element in accordance with the invention are provided with an anti adhesion coating 18 which has self cleaning properties. Furthermore, storage locations for bacteriostatic and/or bactericidal substances are provided at the securing element and inside the cover. Storage locations of this kind (not illustrated) can for example be provided in the form of depressions or cavities.

Figure 4:
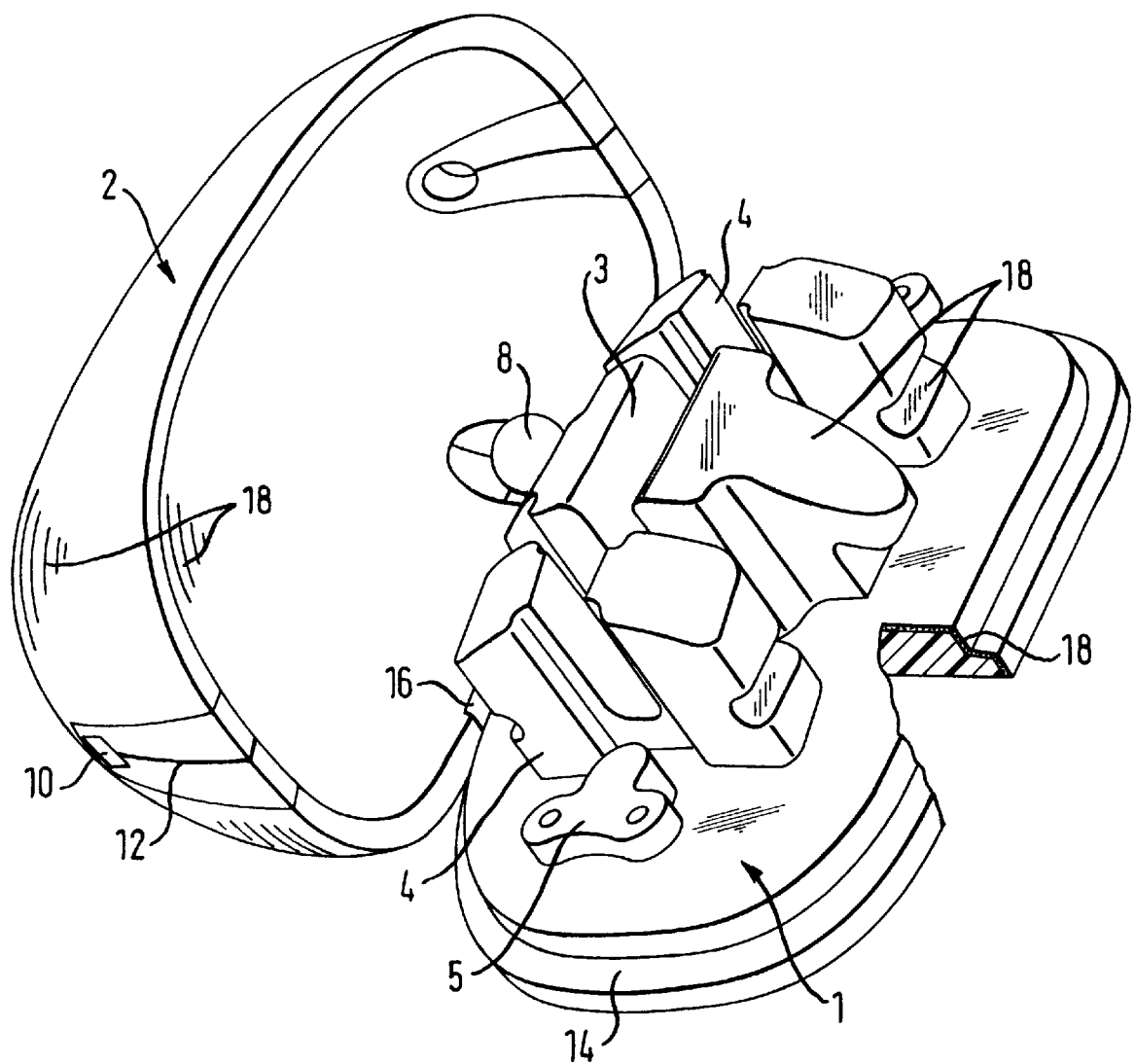
FIG. 4 the securing element of FIG. 1 with a hingably secured cover.

In addition to the illustrated exemplary embodiment it is also possible that the cover also completely covers over the base at its outer edge. Furthermore, as seen in FIG. 4 the cover 2 may be secured by a hinge 16 to the base 1.

It should again be emphasized that the present invention is not restricted to a securing element, but also comprises a cover which is suitable for a subsequent equipping of conventional brackets.

What is claimed is:

1. An orthodontic bracket for orthodontic therapy comprising a base and a holder for a bow, said holder being arranged on said base, said bracket comprising a removable cover secured to the base and covering over the base and the holder, an outer surface of the cover being convexly arched and having an edge, with a contour of the edge of the cover generally corresponding to an outer contour of the base wherein the base has a circumferential ledge at its outer periphery, onto which the cover is placed.

2. Securing element in accordance with claim 1, wherein the contour of the edge of the cover generally corresponds to the outer contour of the base.

3. Securing element in accordance with claim 1, wherein the base has a circumferential ledge at its outer periphery for placing the cover on.

4. Securing element in accordance with claim 1, wherein the cover is hingably secured to the base.

5. Securing element in accordance with claim 1, wherein at least one registering aid is arranged at the holder for an optical measurement.

6. Securing element in accordance with claim 1, wherein the holder has at least one hook which is movable beyond the outer contour of the base.

7. Securing element in accordance with claim 1, wherein said securing element has a connection mechanism for securing at a palate bow.

8. Securing element in accordance with claim 1, wherein at least the outer surface of the cover has self cleaning properties and has an anti adhesion coating, of a sol-gel material.

9. Securing element in accordance with claim 1, wherein the entire securing element has an anti adhesion coating.

10. Securing element in accordance with claim 1, wherein storage locations for bacteriostatic and/or bactericidal substances are provided within the cover.

* * * * *